(12) United States Patent
Lemasters et al.

(10) Patent No.: US 9,970,947 B2
(45) Date of Patent: May 15, 2018

(54) FLUORESCENT PROBE

(71) Applicant: MUSC FOUNDATION FOR RESEARCH DEVELOPMENT, Charleston, SC (US)

(72) Inventors: John J. Lemasters, Johns Island, SC (US); Andaleb I. Kholmukhamedov, Milwaukee, WI (US); Christopher Lindsey, Wadmalaw Island, SC (US); Craig C. Beeson, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 0 days. days.

(21) Appl. No.: 15/472,414

(22) Filed: Mar. 29, 2017

(65) Prior Publication Data

US 2017/0285045 A1    Oct. 5, 2017

Related U.S. Application Data

(60) Provisional application No. 62/315,825, filed on Mar. 31, 2016.

(51) Int. Cl.
*G01N 33/84* (2006.01)
*C09B 11/08* (2006.01)
(Continued)

(52) U.S. Cl.
CPC ......... *G01N 33/84* (2013.01); *A61K 49/0043* (2013.01); *C09B 11/08* (2013.01);
(Continued)

(58) Field of Classification Search
CPC ..................................................... G01N 33/84
(Continued)

(56) References Cited

U.S. PATENT DOCUMENTS

2009/0253161 A1\* 10/2009 Franz ..................... C07F 5/025
435/29

\* cited by examiner

*Primary Examiner* — Paul W Dickinson

(57) ABSTRACT

Provided herein is a fluorescent probe compound of formula (I):

(Continued)

(I)
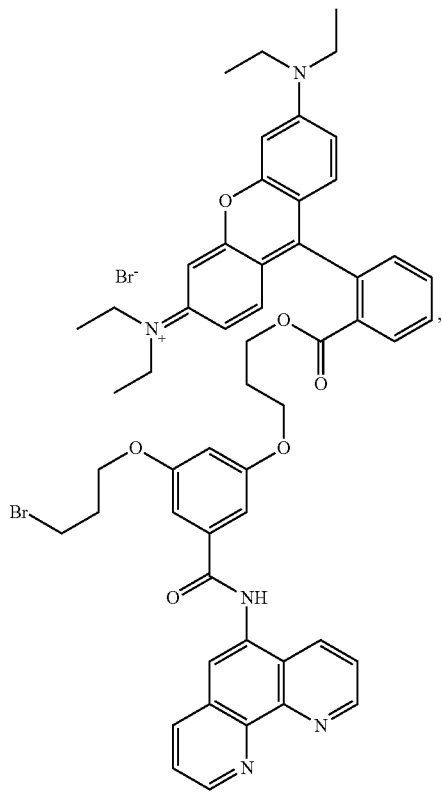
as well as methods of using said compound.
5 Claims, 6 Drawing Sheets
(51) Int. Cl.
*G01N 21/64* (2006.01)
*A61K 49/00* (2006.01)
*G01N 33/58* (2006.01)
(52) U.S. Cl.
CPC ....... *G01N 21/6428* (2013.01); *G01N 33/582* (2013.01); *G01N 2021/6432* (2013.01); *G01N 2021/6439* (2013.01); *G01N 2800/7009* (2013.01); *G01N 2800/7019* (2013.01)
(58) Field of Classification Search
USPC ........................................................ 424/400
See application file for complete search history.

FLUORESCENT PROBE

STATEMENT REGARDING FEDERALLY SPONSORED RESEARCH OR DEVELOPMENT

This invention was made with Government support under NIGMS/NIH DK073336 and NIH/NIDDK DK37034. The Government has certain rights in the invention.

FIELD OF THE INVENTION

The invention is directed to a novel fluorescent indicator useful, for example, for measuring mitochondrial chelatable iron in living cells and tissues.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Iron is an essential nutrient. Incorporation of iron into prosthetic groups (e.g., heme, sulfur-iron clusters) occurs exclusively in the mitochondrial matrix. Mitochondrial chelatable iron contributes to reactive oxygen species (ROS) formation in several pathophysiological settings, including ischemia/reperfusion and acetaminophen hepatotoxicity. Previous studies show that bafilomycin, ischemia and other stresses cause lysosomes to release $Fe^{2+}$ and that this iron is subsequently taken up into mitochondria to promote ROS formation.

A need, therefore, exists in the art for fluorescence probes to measures chelatable iron in the mitochondrial matrix useful to researchers studying iron metabolism, for example to assess the mitochondrial chelatable iron pool when mitochondrial membrane potential ($\Delta\Psi$) is compromised as during cardiovascular events such as, for example, ischemia.

SUMMARY OF THE INVENTION

The present invention is directed to a fluorescent probe compound of formula (I) (referred to herein as mitoferrofluor or "MFF"):

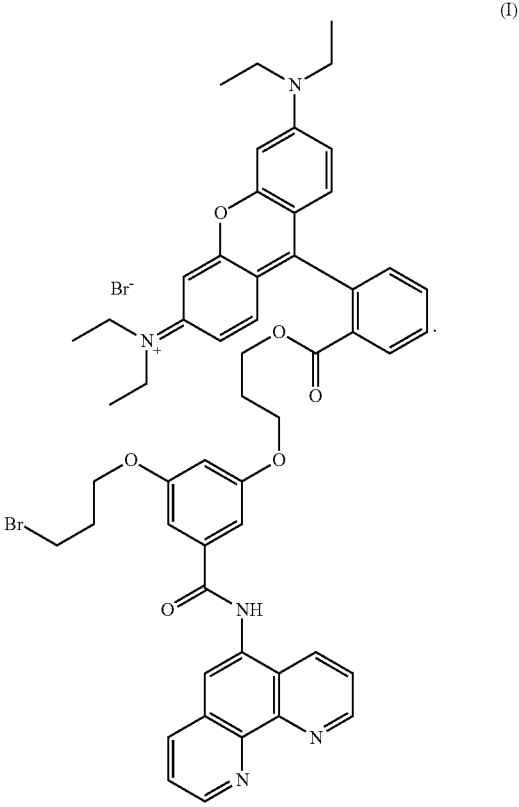

The present invention is also directed to a method of detecting the presence or absence of iron in a cell or composition using the fluorescent probe compound of formula (I). The present invention is further directed to a method for monitoring cardiovascular and other organ system events by using the fluorescent probe compound of formula (I).

DETAILED DESCRIPTION OF THE INVENTION

Figure 1:
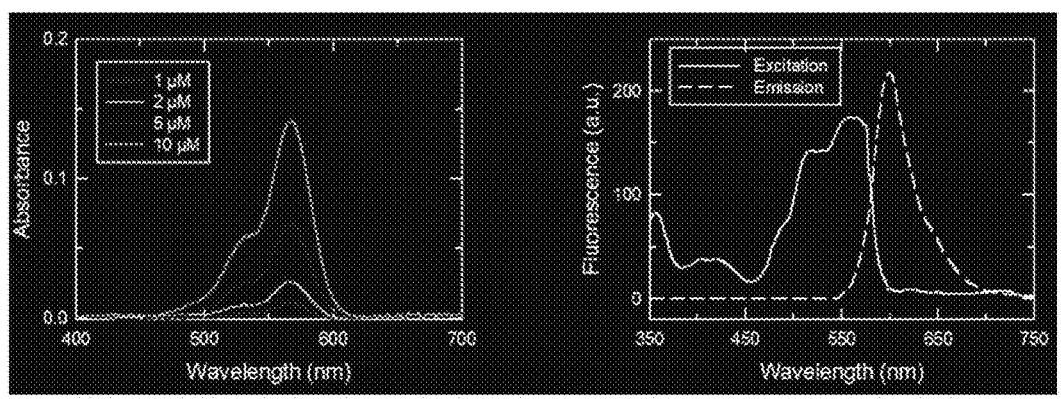
FIG. 1 is a graph which shows the absorption, excitation and emission spectra of mitoferrofluor.

It is to be understood that the descriptions of the present invention have been simplified to illustrate elements that are relevant for a clear understanding of the present invention, while eliminating, for the purpose of clarity, many other elements found in typical pharmaceutical compositions.

Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

Provided herein is a new fluorescent indicator MFF to measure mitochondrial chelatable iron in living cells and tissues. MFF is a cationic fluorophore designed to accumulate electrophoretically into the matrix space of polarized mitochondria. MFF was further designed to have a reactive group that forms covalent adducts with mitochondrial proteins to allow retention of MFF after subsequent mitochondrial depolarization.

MFF fluorescence showed excitation and emission peaks at 554 and 598 nm, respectively. In cell free medium, MFF fluorescence was strongly and stoichiometrically quenched by $Fe^{2+}$ but not by $Fe^{3+}$. In cultured rat hepatocytes, MFF selectively accumulated into mitochondria. Unlike the membrane potential ($\Delta\Psi$) indicator rhodamine 123, MFF was retained by mitochondria after collapsing $\Delta\Psi$ by uncoupler (10 μM CCCP) in the presence of inhibitors of the mitochondrial ATP synthase (10 μg/ml oligomycin) and respiratory Complex III (10 μM myxothiazol).

In MFF-loaded hepatocytes, intramitochondrial MFF fluorescence decreased by ~80% when excess extracellular $Fe^{2+}$ was added. In conclusion, MFF retention by mitochondria is independent of mitochondrial $\Delta\Psi$ unlike earlier mitochondrial iron indicators, such as rhodamine B-[(1,10-phenanthrolin-5-yl)aminocarbonyl]benzyl ester (RPA). Thus, MFF can be used to determine mitochondrial chelatable iron in normal hepatocytes with polarized mitochondria as well as in cells undergoing loss of mitochondrial membrane potential as in case of ischemia or an ischemic event.

An ischemic event refers to an event in which the blood supply to a tissue is obstructed. Due to this obstruction, the endothelial tissue lining the affected blood vessels becomes "sticky" and begins to attract circulating white blood cells. The white cells bound to the endothelium eventually migrate into the affected tissue, causing significant tissue destruction. Although neither acute myocardial infarction nor stroke is directly caused by inflammation, much of the underlying pathology and the damage that occurs after an acute ischemic event are caused by acute inflammatory responses during reperfusion, the restoration of blood flow to the affected organ. Early restitution of blood flow to ischemic tissues is essential to halt the progression of cellular injury associated with decrease of oxygen supply and nutrient delivery. This fact provides the basis for the traditional view that minimizing ischemic time is the only important intervention for diminishing the extent of ischemic injury. However, it is now well recognized that reperfusion of ischemic tissues initiates a complex series of reactions that can paradoxically injure tissues. Although several mechanisms have been proposed to explain the pathogenesis of ischemia-reperfusion injury, most attention has focused on a role for reactive oxygen and nitrogen metabolites and inflammatory leukocytes. In addition to the local tissue injury, distant organs can also be affected, particularly if the intensity of the inflammatory reaction in post-ischemic tissue (e.g., heart, intestine, liver) is great. The remote effects of ischemia-reperfusion injury are most frequently observed in the lung and (cardio- or cerebro-) vascular system, and can result in the development of the systemic inflammatory response syndrome (SIRS) and multiple organ dysfunction syndrome (MODS), both of which account for 30-40% of the mortality in tertiary referral intensive care units (ICUs).

Thus, in one embodiment of the invention, provided is a fluorescent probe compound of formula (I):

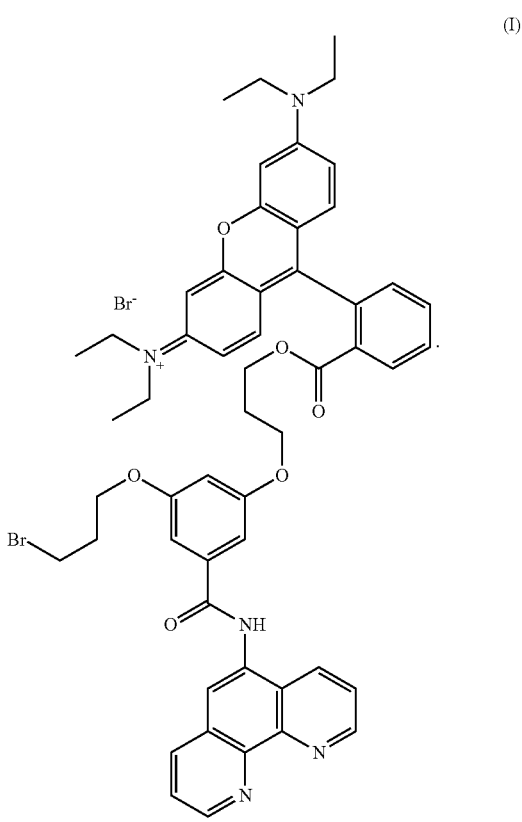

(I)

In another embodiment of the present invention, provided is a method of detecting the presence or absence of iron in a cell or composition, comprising the steps of: administering the fluorescent probe compound of formula (I) to a cell or composition; exciting said fluorescent probe compound of formula (I); and detecting the presence or absence of emission from said fluorescent probe compound of formula (I), wherein emission from said fluorescent probe compound of formula (I) is quenched by the presence of iron in said cell or composition.

In a further embodiment of the present invention, provided is a method for monitoring a cardiovascular or other organ system event, comprising the steps of: administering the fluorescent probe compound of formula (I) of claim 1 to a patient in need thereof; exciting said fluorescent probe compound of formula (I); and detecting the presence or absence of emission from said fluorescent probe compound of formula (I), wherein emission from said fluorescent probe compound of formula (I) is quenched by the presence of iron in said cell or composition.

In one embodiment, the cardiovascular event is ischemia.

In a still further embodiment of the present invention, provided is a kit comprising a fluorescent probe compound of formula (I), and/or instructions for carrying out a method of detecting the presence or absence of iron therewith, optionally in a common package or container.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

It will also be appreciated that a compound according to the invention is inherently intended to comprise all stereochemically isomeric forms thereof. The term "stereochemically isomeric forms" as used hereinbefore or hereinafter defines all the possible stereoisomeric forms which the compounds of formula (I), and their N-oxides, pharmaceutically acceptable salts or physiologically functional derivatives may possess. Unless otherwise mentioned or indicated, the chemical designation of compounds denotes the mixture of all possible stereochemically isomeric forms. In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art. Stereochemically isomeric forms of the compounds of formula (I) are, thus, obviously intended to be embraced within the scope of this invention. Of special interest are those compounds of formula (I) which are stereochemically pure.

The invention will now be further described in the Examples below, which are intended as an illustration only and do not limit the scope of the invention.

EXAMPLES

Reactions were monitored by analytical thin-layer chromatography on EM-Science hard layer silica gel-60E-254 plates cut into 1×2.5 cm pieces or using an Agilent 1100 LCMS. Visualization was effected by ultraviolet light (254 nm), followed by staining the plate and drying on a hot plate. The stain was made with [25 grams of phosphomolybdic acid, 10 grams of cerium sulfate, 60 mL $H_2SO_4$, and 940 mL $H_2O$. The potassium permanganate stain was made with [200 mL $H_2O$, 1.33 grams $KMnO_4$, 13.33 grams of $K_2CO_3$ and 4 mL of 5% NaOH]. Chromatography was performed either by Teledyne ISCO or following the method prescribed by W. C. Still. In reactions where water was not present by solvent, reagent or by-product, the vessels were flame-dried or stored in an oven at 160° C. then cooled under a slow argon flow. A slight positive pressure of dry argon was maintained via rubber septa seal during the course of the reaction. The argon stream originated from a regulated high-pressure argon tank and was used without further drying. All reactions were stirred with a Teflon-coated magnetic stir bar and stir plate. Removal of solvents was typically done using a Buchi rotary evaporator, Model number 114 connected to house vacuum line. The condenser was cooled by a Haake B3 circulator chilled to 0° C. cold thumb. All reaction solvents were purchased as anhydrous with sure seal tops. $^1$H-NMR spectra were recorded at 400 MHz on a Bruker spectrometer. $^{13}$C-NMR were recorded at (100 MHz) with a solvent resonance of 77.23 ppm. All chemical shifts were reported from tetramethylsilane with the solvent resonance of $CDCl_3$ (7.27 ppm), DMSO-d6 (2.5 ppm). Mass spectra were recorded on a Agilent 1100 LCMS using an Agilent 6120 API/APCI multimode source. Reverse phase analytical runs were done on an Agilent 1100 HPLC (95:5 $H_2O$ w/0.1% formic acid/MeCN—100% MeCN over 10 minutes, with a 3 minute 100% MeCN wash on a Phenomenex Luna 3 micron C18 100 angstrom column 20×4 mm, with a flow rate of 1.0 mL/minute.

Example 1

Synthesis of Probe N-(9-(2-((3-(3-(((1,10-phenanthrolin-5-yl)carbamoyl)-5-(3-bromopropoxy)phenoxy)propoxy)carbonyl)phenyl)-6-(diethylamino)-3H-xanthen-3-ylidene)-N-ethylethanaminium bromide 3,5-bis(3-bromopropoxy)benzoate To an oven dried flask equipped with a reflux condenser that was cooled under argon was added methyl 3,5-dihydroxybenzoate (2.0 grams, 11.9 mmol) potassium carbonate (4.11 grams, 29.8 mmol) and 0.2 L of anhydrous acetone (Acros). After stirring at room temperature for approximately 10 minutes 1,3 dibromopropane (12.0 mL, 119 mmol) was added and the solution was heated to 70° C. The reaction continued to stir at this temperature overnight. The next day the reaction was cooled to room temperature, concentrated, taken up in approximately 100 mL of dichloromethane, filtered and concentrated. Purification was done using a Teledyne ISCO automated chromatography system on silica support using a hexanes/ethyl acetate (9:1) afforded the desired material methyl (2.47 grams, 51% yield).

3,5-bis(3-bromopropoxy)benzoic acid

To a clean dry flask equipped with an air to air condenser was added 3,5-bis(3-bromopropoxy)benzoate (2.47 grams, 6.01 mmol) followed by acetic acid/HBr (12.0 mL). The stirring solution was heated to 60° C. where it stirred overnight. The next day it was cooled to 0° C. to form a precipitate. The precipitate was collected by filtration. The precipitate was rinse two times with hexanes. Once collected the precipitate was placed under vacuum. It was then used without any further purification. MS (ESI negative mode, observed mass 392, M−1).

3,5-bis(3-bromopropoxy)-N-(1,10-phenanthrolin-5-yl)benzamide

To a flame dried flask cooled under argon was added 3,5-bis(3-bromopropoxy)benzoic acid (0.792 grams, 2.0 mmol) and the amino-phenanthroline (0.390 grams, 2.0 mmol). The two compounds were then taken up in 20.0 mL of anhydrous DMF (Aldrich) and HCTU (0.909 grams, 2.2 mmol) was added. After five minutes, diisopropylethylamine (1.1 mL, 6.0 mmol) was added. After five days of stirring at room temperature the reaction was concentrated, taken up in ethyl acetate and washed with sodium bicarbonate (saturated). Upon removal of the organic layer the aqueous was salted out, and washed twice more with ethyl acetate. Confirmation of no residual desired material was done by LCMS of the aqueous layer. Purification was done using a Teledyne ISCO C18 reverse phase chromatography (water with 0.1% formic acid/MeCN gradient) to afford the desired material. Approximate yield, 20% MS (ESI positive mode, observed mass 572, M+1).

Alternate procedure for 3,5-bis(3-bromopropoxy)-N-(1,10-phenanthrolin-5-yl)benzamide To a flame dried flask cooled under argon was added 3,5-bis(3-bromopropoxy)benzoic acid (0.1 grams, 0.25 mmol) and anhydrous dichloromethane (2.0 mL). While stirring at room temperature, oxallyl bromide (60 µL) was added, followed by 8 µL of DMF (anhydrous). After 45 minutes, the reaction was concentrated, and the aminophenanthroline (0.0542 grams, 0.275 mmol) was added. This was followed by the addition of $NaHCO_3$ (0.068 grams, 0.5 mmol) and 20 mL of anhydrous acetonitrile. The reaction was stirred overnight at room temperature. Next, the solution was filtered and the precipitant collected. The remaining solution was concentrated, and also used without any further purification. MS (ESI positive mode, observed mass 572, M+1).

N-(9-(2-((3-(3-(((1,10-phenanthrolin-5-yl)carbamoyl)-5-(3-bromopropoxy)phenoxy) propoxy)carbonyl)phenyl)-6-(diethylamino)-3H-xanthen-3-ylidene)-N-ethylethanaminium bromide. To a flame-dried flask cooled under argon was added 3,5-bis(3-bromopropoxy)-N-(1,10-phenanthrolin-5-yl)benzamide (0.022 grams, 0.038 mmol) and Rhodamine B base (0.0184 grams, 0.038 mmol) followed by 0.4 mL anhydrous DMF. The solution was then heated to 100° C. where it stirred overnight. The next day it was concentrated, taken up in 0.8 mL of methanol and purified using a Teledyne ISCO C18 reverse phase chromatography (water with 0.1% formic acid/MeCN gradient) to afford the desired material. Approximate yield, 10%. MS (ESI positive mode, observed mass 935, M+1).

Example 2

Absorption, Excitation and Emission Spectra of Mitoferrofluor

Absorption, excitation and emission spectra of Mitoferrofluor (MFF) are shown in FIG. 1. The left panel shows the absorbance spectrum for MFF in 10 mM Tris/HCl (pH 8.0 at 23° C.) and 5 mM desferal. The right panel shows excitation and emission spectra of MFF in the presence of 5 mM desferal.

Example 3

Figure 2:
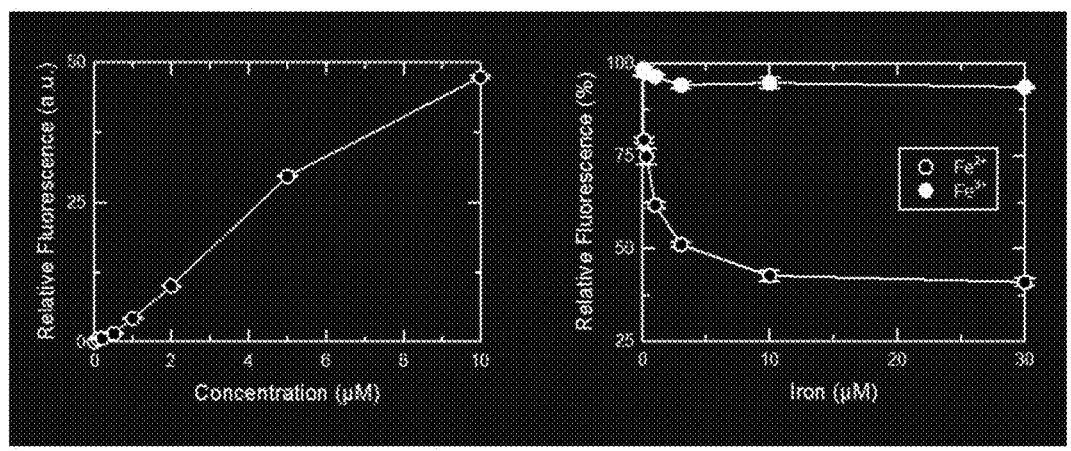
FIG. 2 has graphs showing the relationship of mitoferrofluor fluorescence with mitoferrofluor concentration and $Fe^{2+}$ and $Fe^{3+}$ concentration.

Relationship of Mitoferrofluor Fluorescence with Mitoferrofluor Concentration and $Fe^{2+}$ and $Fe^{3+}$ Concentration MFF (0-10 µM) was dissolved in medium at the presumed intramitochondrial pH (pH 8.0, 37° C.) (FIG. 2, left panel). Fluorescence of MFF (1 µM) was measured as a function of increasing ferrous ammonium sulfate ($Fe^{2+}$) and ferric chloride ($Fe^{3+}$) concentration from freshly prepared stock solutions (1 mM). Fluorescence intensity is shown in arbitrary units (a.u.). (FIG. 2, right panel).

Example 4

Mitoferrofluor Release

Rhodamine 123 (Rh123) and MitoTracker Green (MTG) were obtained from Molecular Probes. Primary rat hepatocytes were isolated from overnight-fasted male Sprague-Dawley rats (200-250 g) by collagenase perfusion. Hepatocytes were plated on Type 1 collagen-coated MatTek dishes at a density of 300,000 cells per well and cultured overnight in Waymouth's MB-742/1 growth medium containing 27 mM $NaHCO_3$, 2 mM L-glutamine, 10% fetal calf serum, 100 nM insulin and 10 nM dexamethasone, pH 7.4 at 37° C. in 5% CO2/air.

Confocal images of hepatocytes were taken with a Zeiss LSM 510 inverted laser scanning confocal microscope (Carl Zeiss, Germany) using a 63×oil immersion objective.

Figure 3:
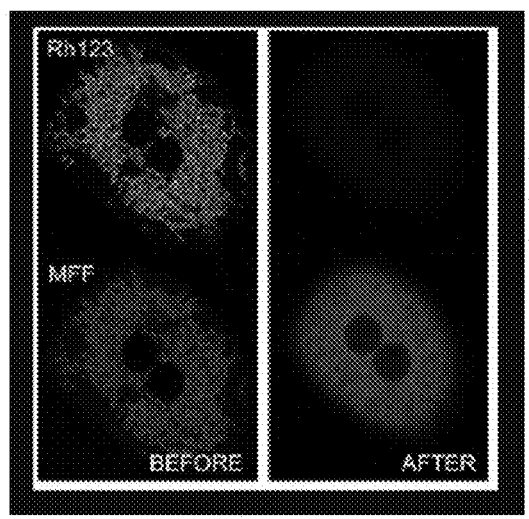
FIG. 3 is an image which indicates that depolarized mitochondria do not release mitoferrofluor.

Overnight-cultured rat hepatocytes were loaded with MFF (1 µM for 20 min), washed and incubated for 60 min. Rh123 was then loaded and the cells then incubated with 5 mM fructose to prevent cell killing after addition of CCCP (10 oligomycin (10 µg/mL) and myxothiazol (10 inhibitors of respiration and oxidative phosphorylation that depolarize mitochondria. As seen in FIG. 3, depolarized mitochondria did not release mitoferrofluor. Unlike ΔΨ-indicating rhodamine 123, MFF was retained by mitochondria after addition of the mitochondrial inhibitors, as shown by confocal fluorescence images collected "BEFORE" and "AFTER" the addition.

Example 5

Figure 4:
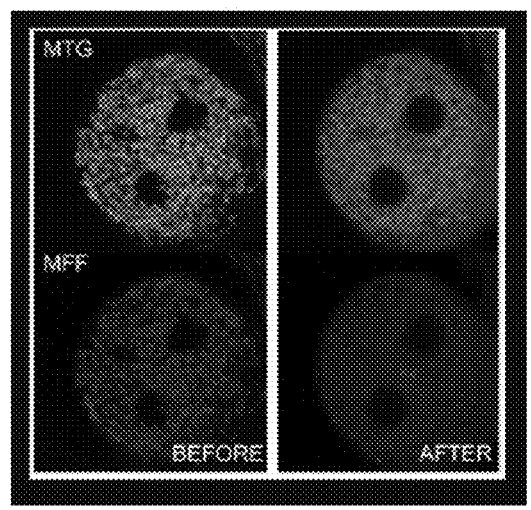
FIG. 4 is an image which shows that mitochondria swell after inhibition of oxidative phosphorylation but retain mitoferrofluor.

Mitochondria Swell after Inhibition of Oxidative Phosphorylation but Retain Mitoferrofluor Overnight-cultured rat hepatocytes were loaded with MFF and MTG (both 1 µM for 20 min), washed and incubated for 60 min. Cells were then incubated with 5 mM fructose and imaged "BEFORE" and "AFTER" addition of CCCP, oligomycin and myxothiazol. MTG fluorescence reveals mitochondrial swelling and some release of MTG into the cytosol (indicating mitochondrial membrane permeabilization). MFF fluorescence changed essentially identically to MTG consistent with covalent labeling of mitochondrial proteins by MFF. FIG. 4 shows that mitochondria swelled after inhibition of oxidative phosphorylation but MFF fluorescence was retained.

Example 6

Mitoferrofluor Quenching After Mitochondrial $Fe^{2+}$ Uptake

Figure 5:
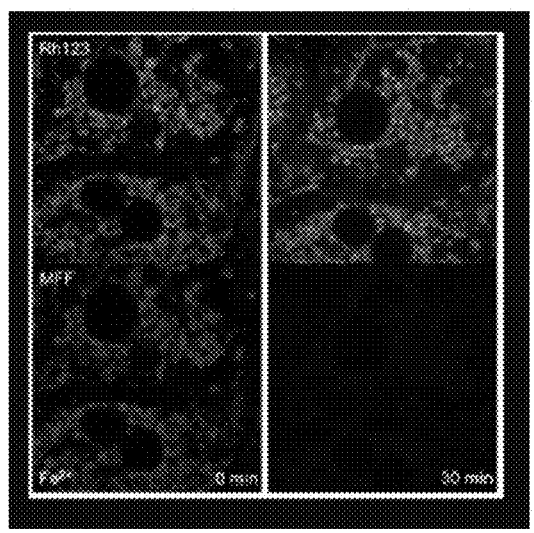
FIG. 5 is an image which shows mitoferrofluor quenching after mitochondrial $Fe^{2+}$ uptake.

Overnight-cultured rat hepatocytes were loaded with MFF (1 µM for 20 min), washed out and incubated for 60 min. Rh123 (0.5 µM for 20 min) was then loaded. $Fe^{2+}$ was added as ferrous ammonium sulfate (10 mM). $Fe^{2+}$ addition quenched MFF fluorescence by ~72%. Results are shown in FIG. 5.

Example 7

Figure 6:
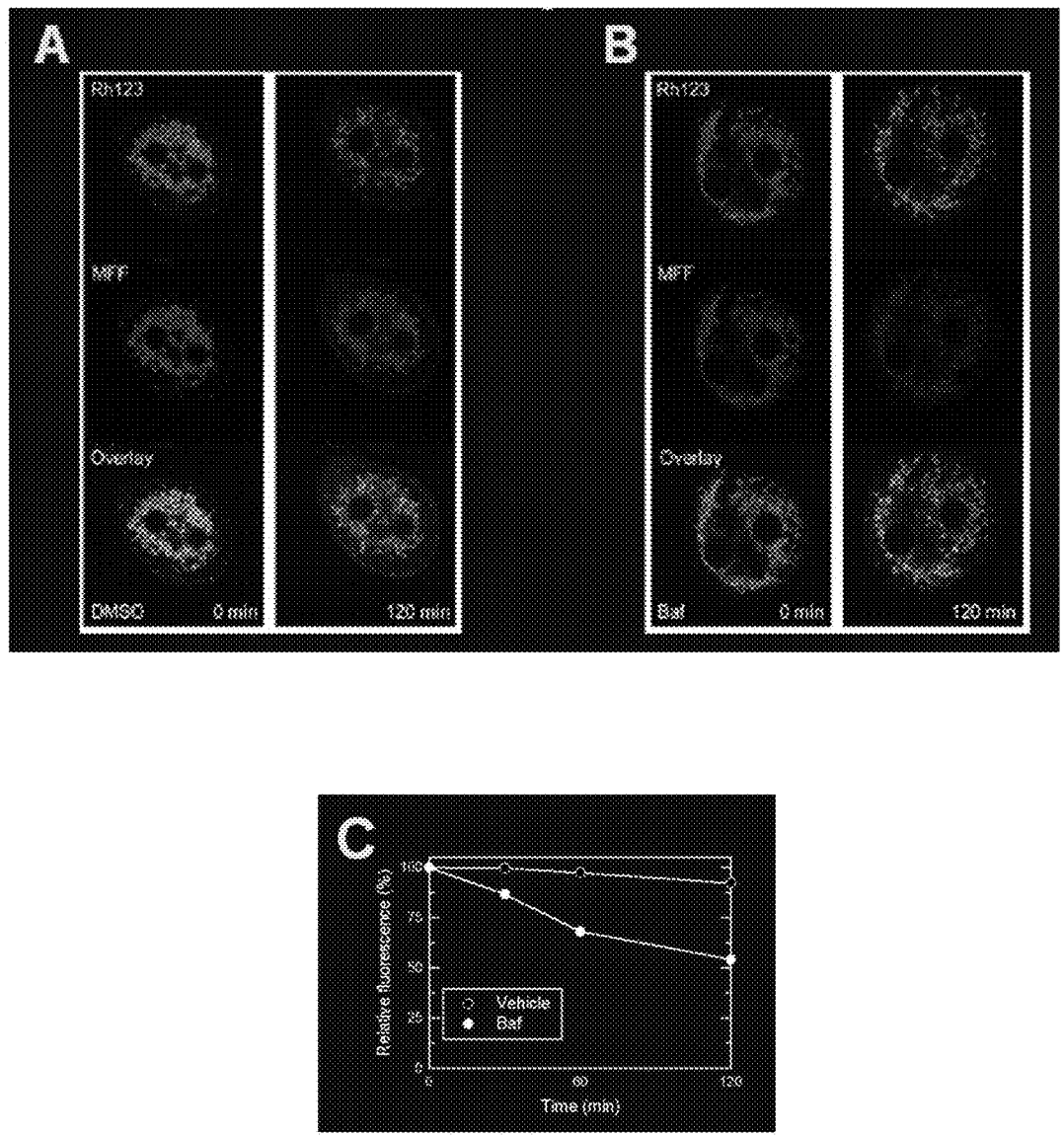
FIG. 6 has images (A and B) and a graph (C) which show mitoferrofluor fluorescence quenching after lysosomal iron release with bafilomycin A1.

Mitoferrofluor Fluorescence Quenching after Lysosomal Iron Release with Bafilomycin Overnight-cultured rat hepatocytes were loaded with MFF and then rhodamine 123, as described in Example 6. Mitochondrial MFF fluorescence became quenched 120 min after the addition of bafilomycin A1 (Baf, panel B) compared to vehicle control (DMSO, panel A). Panel C represents a quantitative analysis of 10 random fields (*$p<0.05$ vs vehicle, n=3). FIG. 6 shows mitoferrofluor fluorescence quenching after lysosomal iron release with bafilomycin A1.

As shown in the above Examples, the extinction coefficient for MMF was 40,400 $cm^{-1}/M$ at 566 nm; $Fe^{2+}$ but not $Fe^{3+}$ quenched MFF fluorescence with an $IC_{50}$ of 1-2 µM; mitochondria retained MFF to the same extent as MTG after mitochondrial depolarization; and exogenous $Fe^{2+}$ and lysosomal $Fe^{2+}$ released after bafilomycin quenched mitochondrial MFF fluorescence in hepatocytes. MFF is, thus, an indicator of mitochondrial chelatable $Fe^{2+}$ in intact hepatocytes in a ΔΨ-independent fashion. Therefore, MFF may be useful to monitor mitochondrial iron pools in pathological conditions, such as ischemia, that induce mitochondrial depolarization.

It is to be understood that the invention is not limited to the particular embodiments of the invention described above, as variations of the particular embodiments may be made and still fall within the scope of the appended claims.

What is claimed is:

1. A fluorescent probe compound of formula (I):

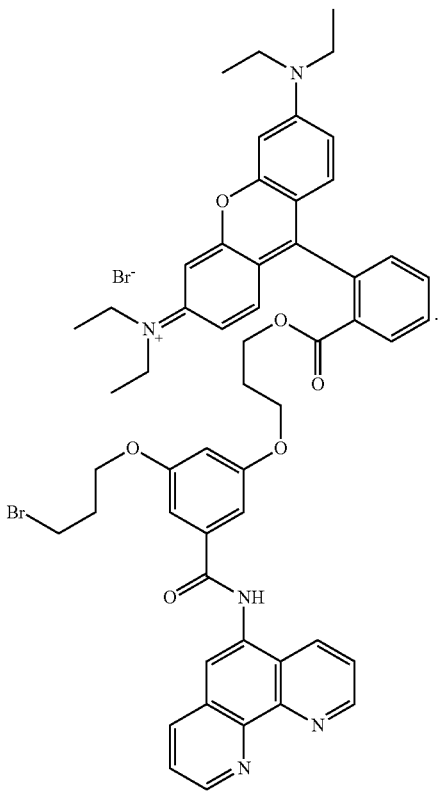

(I)

2. A method for detecting the presence or absence of iron in a cell or composition, comprising the steps of: administering the fluorescent probe compound of formula (I) of claim 1 to a cell or composition; exciting said fluorescent probe compound of formula (I); and detecting the presence or absence of emission from said fluorescent probe compound of formula (I), wherein emission from said fluorescent probe compound of formula (I) is quenched by the presence of iron in said cell or composition.

3. A method for monitoring a cardiovascular or other organ system event, comprising the steps of: administering the fluorescent probe compound of formula (I) of claim 1 to a patient in need thereof; exciting said fluorescent probe compound of formula (I); and detecting the presence or absence of emission from said fluorescent probe compound of formula (I), wherein emission from said fluorescent probe compound of formula (I) is quenched by the presence of iron in said cell or composition.

4. The method of claim 3, wherein said cardiovascular or organ system event is ischemia.

5. A kit comprising a fluorescent probe compound of claim 1, and/or instructions for carrying out a method of detecting the presence or absence of iron or copper therewith, optionally in a common package or container.

* * * * *